US011524110B2

(12) United States Patent
Azapagic et al.

(10) Patent No.: US 11,524,110 B2
(45) Date of Patent: Dec. 13, 2022

(54) INFUSION PUMP LATCH MECHANISM AND ASSOCIATED FREE-FLOW PROTECTION DEVICE

(71) Applicant: Curlin Medical Inc., Elma, NY (US)

(72) Inventors: Azur Azapagic, New Haven, CT (US); Mohan Jonathan Barkley, Salt Lake City, UT (US)

(73) Assignee: Curlin Medical Inc., Elma, NY (US)

( * ) Notice: Subject to any disclaimer, the term of this patent is extended or adjusted under 35 U.S.C. 154(b) by 525 days.

(21) Appl. No.: 16/694,090

(22) Filed: Nov. 25, 2019

(65) Prior Publication Data

US 2020/0086045 A1 Mar. 19, 2020

Related U.S. Application Data

(62) Division of application No. 15/634,143, filed on Jun. 27, 2017, now Pat. No. 10,549,032.

(51) Int. Cl.
*A61M 5/168* (2006.01)
*A61M 5/142* (2006.01)
*A61M 39/10* (2006.01)
*A61M 39/28* (2006.01)

(52) U.S. Cl.
CPC .... *A61M 5/16804* (2013.01); *A61M 5/14216* (2013.01); *A61M 39/10* (2013.01); *A61M 39/28* (2013.01)

(58) Field of Classification Search
CPC .......... A61M 5/16804; A61M 5/14216; A61M 39/10; A61M 39/28; A61M 39/281
See application file for complete search history.

(56) References Cited

U.S. PATENT DOCUMENTS

| 4,344,435 | A | | 8/1982 | Aubin |
| 4,689,043 | A | | 8/1987 | Bisha |
| 4,728,324 | A | | 3/1988 | Steigerwald et al. |
| 5,437,635 | A | | 8/1995 | Fields et al. |
| 5,692,729 | A | | 12/1997 | Harhen |
| 5,704,584 | A | | 1/1998 | Winterer et al. |
| 5,904,668 | A | | 5/1999 | Hyman et al. |
| 6,164,921 | A | * | 12/2000 | Moubayed ............ F04B 43/082 417/474 |

(Continued)

FOREIGN PATENT DOCUMENTS

SE 9202190 L 2/1994

*Primary Examiner* — Laura A Bouchelle
*Assistant Examiner* — John A Doubrava
(74) *Attorney, Agent, or Firm* — Hodgson Russ LLP (57) ABSTRACT

An infusion pump apparatus includes a length of resilient tubing removably loadable in an infusion pump having a housing, a pumping mechanism, and a pump door. A latch member is pivotally mounted to the pump door and cooperates with a latch pin fixed on pump housing. A free-flow protection device is biased to pinch the tubing closed to stop fluid flow. The latch member has a first range of pivotal motion in a latching direction for causing the latch member to engage with the latch pin to secure the door in a closed position and a second range of pivotal motion in the latching direction for causing the latch member to actuate the free-flow protection device to unpinch the tubing and allow flow. The latch member pivots through at least a portion of the first range of pivotal motion before beginning to pivot through the second range of pivotal motion.

18 Claims, 8 Drawing Sheets

(56) References Cited

U.S. PATENT DOCUMENTS

| | | |
|---|---|---|
| 6,261,262 B1 | 7/2001 | Briggs et al. |
| 6,883,773 B1 | 4/2005 | Mattheis |
| 7,028,727 B1 | 4/2006 | Blair |
| 8,387,943 B1 | 3/2013 | Mattheis |
| 2002/0147425 A1 | 10/2002 | Briggs et al. |
| 2002/0165503 A1 | 11/2002 | Morris et al. |
| 2007/0269324 A1 | 11/2007 | Goldor et al. |
| 2009/0087327 A1 | 4/2009 | Voltenburg et al. |
| 2009/0254034 A1 | 10/2009 | Beck et al. |
| 2010/0036322 A1 | 2/2010 | Rotem |
| 2012/0257986 A1* | 10/2012 | Momeni ................ F04B 43/12 417/477.1 |
| 2013/0336814 A1 | 12/2013 | Kamen et al. |
| 2017/0348197 A1 | 12/2017 | Dormann |

* cited by examiner

INFUSION PUMP LATCH MECHANISM AND ASSOCIATED FREE-FLOW PROTECTION DEVICE

CROSS-REFERENCE TO RELATED APPLICATIONS

The present application is a division of co-pending U.S. application Ser. No. 15/634,143 filed Jun. 27, 2017, the entire disclosure of which is hereby incorporated by reference in the present application.

FIELD OF THE INVENTION

The present invention relates to a latch mechanism for securely closing a door or platen member of an infusion pump, and to a free-flow protection device cooperating with the latch mechanism.

BACKGROUND OF THE INVENTION

Programmable infusion pumps are used to carry out controlled delivery of liquid food for enteral feeding and medications for various purposes such as pain management. In a common arrangement, an infusion pump receives a disposable administration set comprising flexible tubing having a tubing segment designed to be engaged by a pumping mechanism of the infusion pump. The administration set may further comprise a pair of mounting components fixedly attached to the flexible tubing at predetermined locations at or near opposite ends of the tubing segment, whereby the mounting components are receivable by respective mating features on the infusion pump to secure the tubing segment in proper position for operative engagement by the pumping mechanism. One of the mounting components may provide additional functionality beyond helping to properly locate the tubing segment. For example, one of the mounting components may be configured as a free-flow protection device operable to selectively stop and permit flow of the infusion liquid through the tubing. Upon loading the administration set in the pump, the free-flow protection device is actuated from its normal flow-stopping closed position to its open position allowing flow. An example of the arrangement described above is disclosed in U.S. Pat. No. 6,164,921 to Moubayed et al.

In prior art arrangements, a door or platen member of the pump pivots into a closed position after the administration set is loaded. During closure, the door or platen member actuates the free-flow protection device from its closed position to its open position. For example, the free-flow protection device may include a valve body and a plunger spring-biased to pinch the tubing closed, and the door or platen member may engage the plunger and move the plunger against the spring bias to open flow in the tubing. Once the door or platen member is fully closed, the pumping mechanism takes over for the opened free-flow protection device to prevent unintended flow through the tubing.

With this type of arrangement, the free-flow protection device begins to open before the door or platen member is completely closed, and before the pumping mechanism can prevent flow. Consequently, there is a risk that liquid may be infused into the patient by gravity rather than by programmed action of the pumping mechanism when the door or platen member is slightly ajar.

SUMMARY OF THE INVENTION

The present disclosure provides a free-flow protection device and a latch mechanism designed to actuate the free-flow protection device only after a door of an infusion pump is fully closed. The free-flow protection device may be part of a disposable administration set that includes a length of resilient tubing, and the free-flow protection device may be biased to pinch the resilient tubing closed to stop fluid flow therethrough. In one embodiment, the pump door closes over a pumping mechanism of the infusion pump and defines a platen surface opposing the pumping mechanism, and the latch mechanism includes a latch member and a corresponding latch pin, wherein the latch member is pivotally mounted to the pump door and the latch pin is at a fixed location relative to the pump housing. The latch member has a first range of pivotal motion about the latch pivot axis in a latching direction for causing the latch member to engage with the latch pin to secure the pump door in the closed position and a second range of pivotal motion about the latch pivot axis in the latching direction for causing the latch member to actuate the free-flow protection device against the bias to unpinch the resilient tubing and allow fluid flow therethrough, wherein the latch member pivots through at least a portion of the first range of pivotal motion before beginning to pivot through the second range of pivotal motion.

The free-flow protection device may comprise a body, a plunger, and a biasing spring. The body may define a tubing guideway and a plunger channel intersecting the tubing guideway, the plunger being slidably received by the plunger channel. The plunger may define a tubing passageway through the plunger, and the plunger may be movable relative to the body to vary a degree of alignment between the tubing passageway and the tubing guideway. The spring may be arranged to bias the plunger in a direction reducing the degree of alignment between the tubing passageway and the tubing guideway for normally pinching the resilient tubing closed. The plunger may include a curved actuating surface protruding from the plunger channel that is acted upon by a curved cam surface of the latch member to actuate the plunger, thereby opening the free-flow protection device to allow flow through the tubing.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
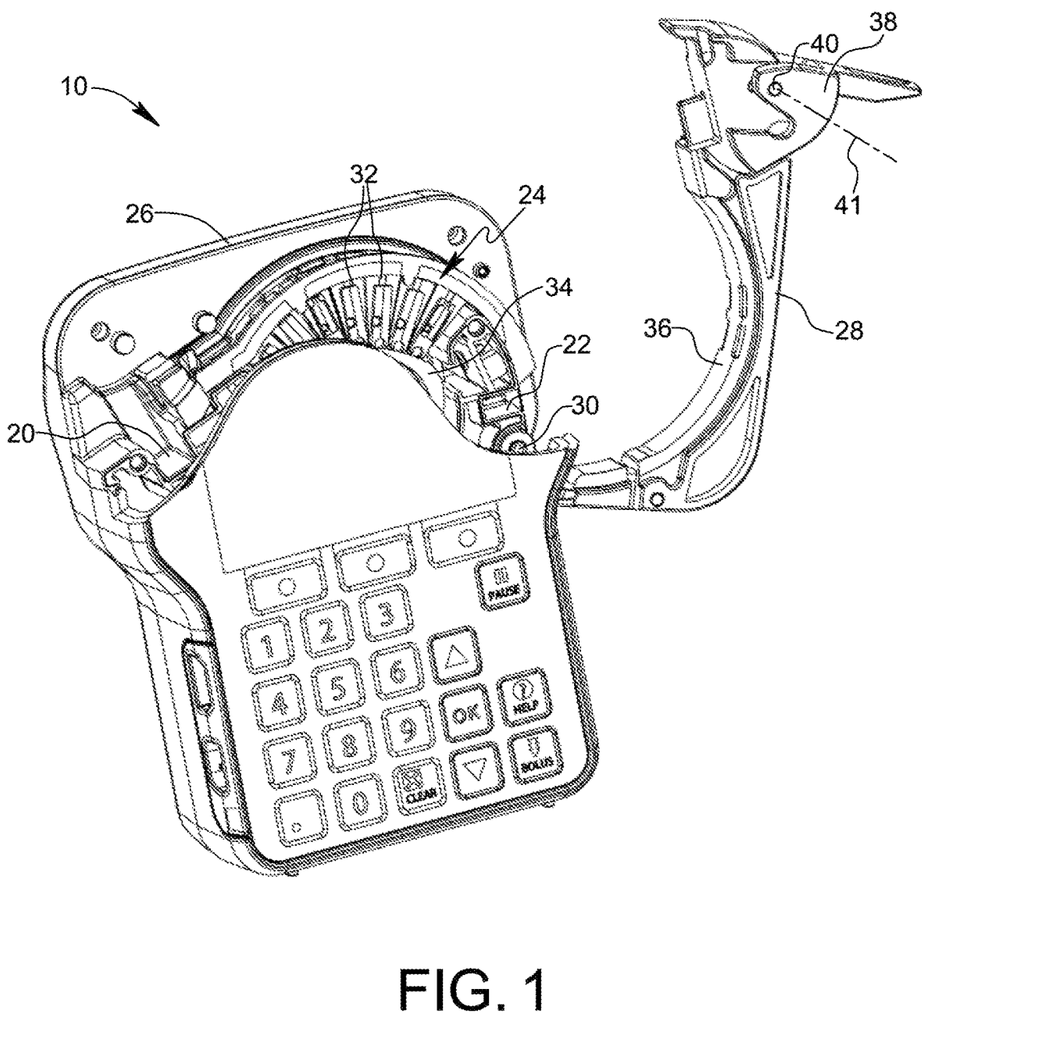
FIG. 1 is a perspective view showing an infusion pump formed in accordance with an embodiment of the present invention.
Figure 2:
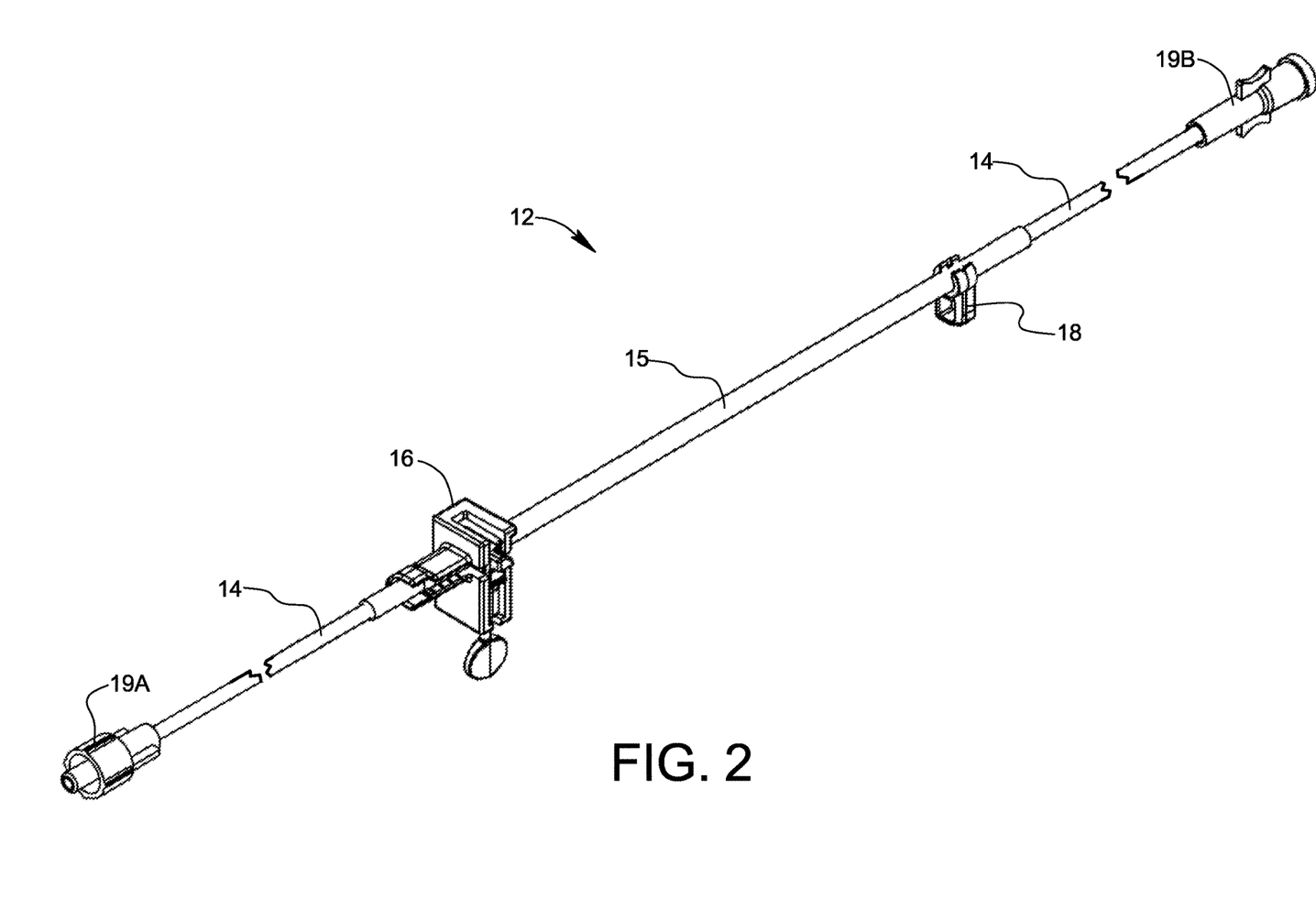
FIG. 2 is a perspective view of an administration set formed in accordance with an embodiment of the present invention.

FIG. 1 shows an infusion pump 10 and FIG. 2 shows a disposable administration set 12 designed to be removably received by infusion pump 10. Administration set 12 comprises tubing 14 for conveying an infusion liquid, and a free-flow protection device 16 operable to selectively stop and permit flow of the infusion liquid through the tubing 14. Administration set 12 may also comprise a locator pin 18. Free-flow prevention device 16 and locator pin 18 may be fixedly attached to tubing 14 at separate locations along the tubing. For example, free-flow prevention device 16 and locator pin 18 may be bonded to tubing 14 by a bonding agent. Administration set 12 may also include a pair of connectors 19A, 19B, one at each end of tubing 14.

In the illustrated embodiment, infusion pump 10 has a first recess 20 sized to removably receive free-flow protection device 16, and a second recess 22 sized to removably receive locator pin 18. Administration set 12 is loaded into infusion pump 10 by inserting free-flow prevention device 16 into first recess 20 and locator pin 18 into second recess 22 such that a segment 15 of tubing 14 is adjacent a pumping mechanism 24 supported by a housing 26 of pump 10.

As may be seen in FIG. 1, infusion pump 10 includes a door 28 movable relative to housing 26 to an open position to allow tubing segment 15 to be loaded in the infusion pump adjacent to pumping mechanism 24 and to a closed position covering the tubing segment 15. In the illustrated embodiment, door 28 is pivotally mounted to housing 26 at a hinge pin 30, however door 28 may be slidably mounted to housing 26 without straying from the invention. As shown in the figures, pumping mechanism 24 may be a curvilinear peristaltic pumping mechanism having a plurality of extendable and retractable pumping fingers 32 that are moved by rotation of a motor-driven eccentric cam 34 to engage and temporarily deform tubing segment 15 in sequential peristaltic fashion such that liquid is pumped through tubing 14. Pumping mechanism 24 may take other forms, such as a linear peristaltic pumping mechanism having axially spaced fingers moved by respective cams mounted on a rotary shaft, or a rotary pumping mechanism having a motor-driven rotor about which tubing segment 15 is partially wound for engagement by pumping elements on the rotor. Where pumping mechanism 24 is a peristaltic pumping mechanism, door 28 may include a platen surface 36 that comes into contact with tubing segment 15 opposite pumping fingers 32 when door 28 is in its closed position.

Infusion pump 10 further includes a latch member 38 pivotally mounted to pump door 28 by a pivot pin 40 for rotation about a transversely-extending latch pivot axis 41 defined by pivot pin 40. Pump 10 also includes a latch pin 42 mounted to project inwardly from a front wall of pump housing 26, wherein latch pin 42 is situated at a fixed location relative to pump housing 26. As will be described in detail below, latch member 38 is operable to secure pump door 28 in its closed position on infusion pump 10 and actuate free-flow protection device 16 to allow fluid flow through tubing segment 15.

Figures 3, 4:
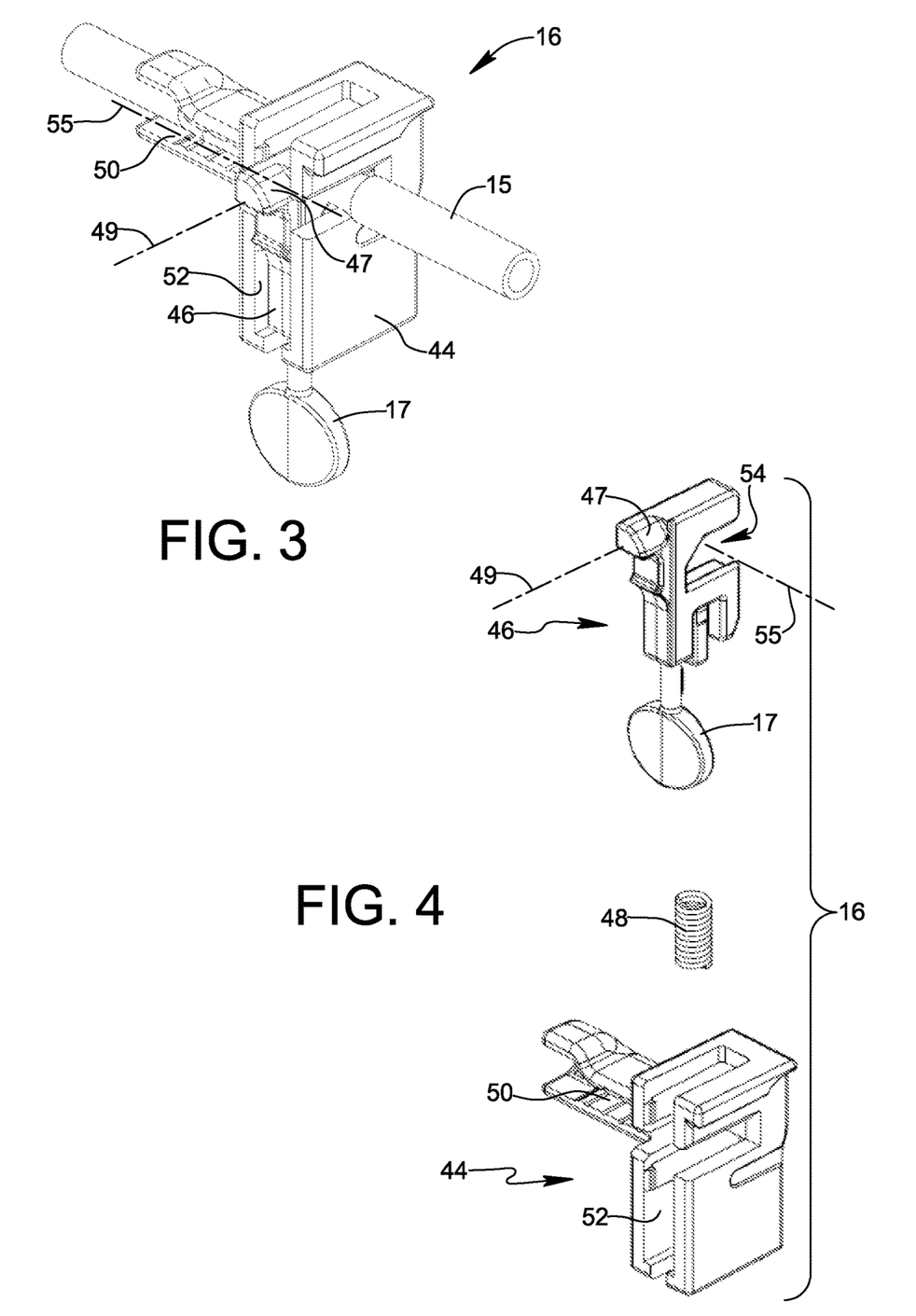
FIG. 3 is a detailed perspective view showing a free-flow protection device of the administration set shown in FIG. 2.
FIG. 4 is an exploded perspective view of the free-flow protection device.

An embodiment of free-flow protection device 16 is shown in detail in FIGS. 3 and 4. Free-flow protection device 16 generally includes a body 44, a plunger 46, and a biasing spring 48. Body 44 defines a tubing guideway 50 and a plunger channel 52 intersecting the tubing guideway. Plunger 46 is slidably received by plunger channel 52, and defines a tubing passageway 54 extending along an axis 55 through the plunger. Plunger 46 is movable relative to body 44 to vary a degree of alignment between tubing passageway 54 of plunger 46 and tubing guideway 50 of body 44. Spring 48 is arranged to bias plunger 46 in a direction reducing the degree of alignment between tubing passageway 54 and the tubing guideway 50. As may be understood, the bias of spring 48 causes resilient tubing segment 15 to be pinched closed by body 44 and plunger 46, thereby preventing flow of infusion liquid through the tubing segment. Plunger 46 may include a curved actuating surface 47. In the example embodiment described herein, curved actuating surface 47 includes an arc segment profile about an axis 49 which is orthogonal to axis 55 of tubing passageway 54. Free-flow protection device 16 may include a breakaway detent tab 17 for maintaining free-flow prevention device 16 in an open condition against the bias of spring 48 while administration set 12 is shipped and stored prior to actual use, wherein breakaway detent tab 17 is permanently removed just prior to loading administration set 12 in pump 10.

Figure 5A:
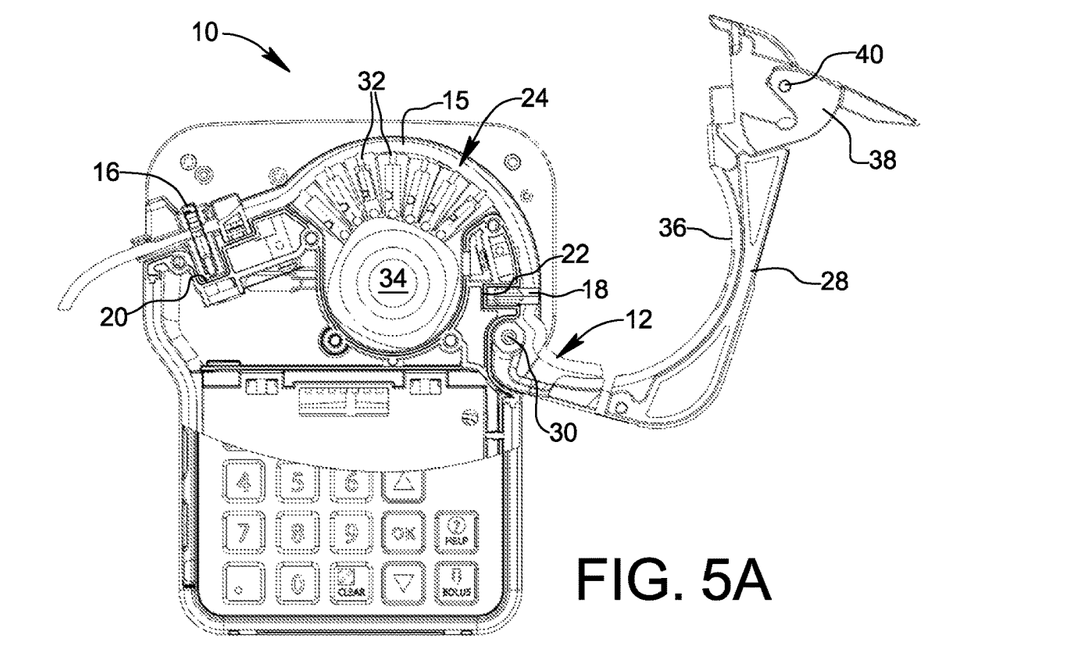
FIGS. 5A and 5B are sectioned front views showing the administration set loaded into the infusion pump before a door of the infusion pump is secured in a closed position.
Figure 5B:
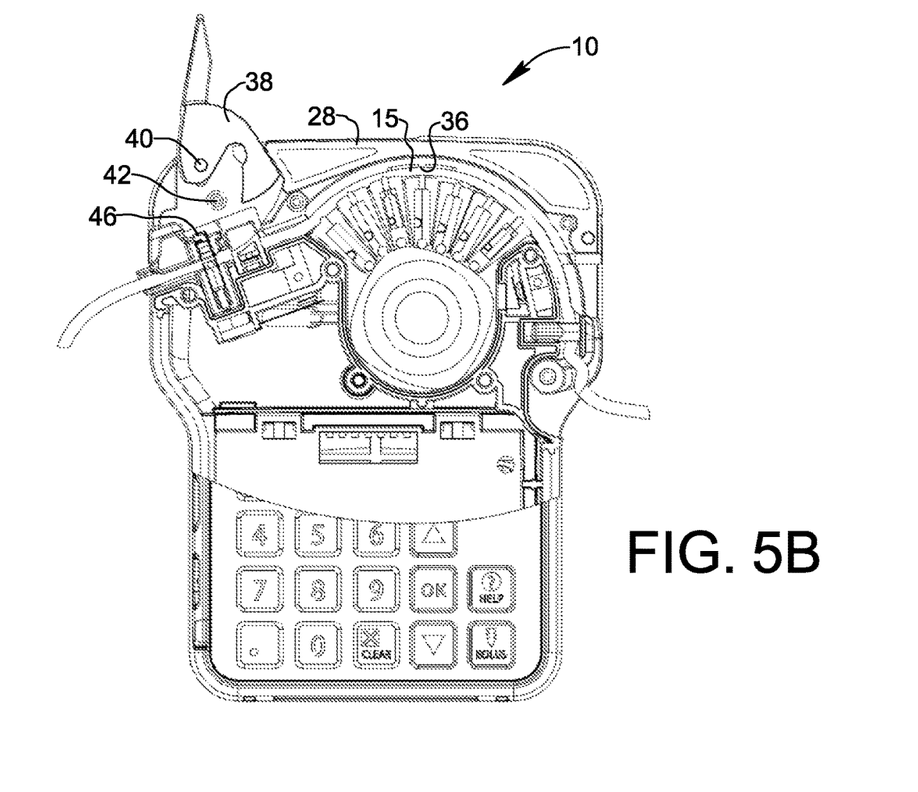

FIGS. 5A and 5B are sectioned front views of pump 10 showing administration set 12 loaded into infusion pump 12 before pump door 28 is secured in its closed position. As shown in FIG. 5A, door 28 may be pivoted about an axis of hinge pin 30 to an open position allowing a user to insert free-flow protection device 16 into first recess 20 and locator pin 18 into second recess 22 such that tubing segment 15 is held in slight tension adjacent pumping fingers 32 of pumping mechanism 24. FIG. 5B shows partial closure of door 28 after administration set 12 is loaded in the pump. Door 28 is almost in its fully closed position in FIG. 5B, but it has not yet been secured in its fully closed position. Door 28 does not contact free-flow protection device 16 before or after door 28 is closed, such that flow protection device 16 operates completely independently of door 28. Therefore, tubing segment 15 remains pinched closed due to the biasing action of spring 48 acting between body 44 and plunger 46. Closure of door 28, whether full or partial, does not actuate free-flow protection device 16 to open flow through tubing segment 15. Rather, as explained below, operation of latch member 38 actuates free-flow protection device 16 to open flow through tubing segment 15.

Figure 6A:
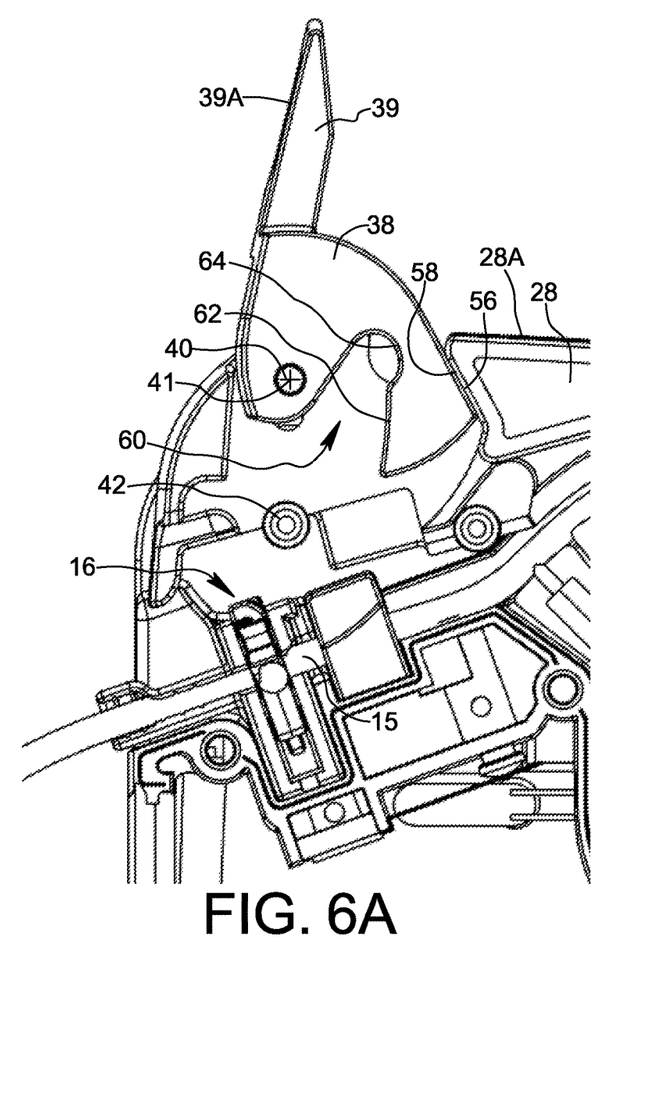
FIGS. 6A through 6F are a series of detailed views showing pivot operation of a latch member of the infusion pump to secure the pump door in a closed position and actuate the free-flow protection device to permit flow.

Reference is now made to FIGS. 6A-6F to describe operation of latch member 38 to secure pump door 28 in its closed position on infusion pump 10 and actuate free-flow protection device 16 to allow fluid flow through tubing segment 15. In FIG. 6A, door 28 is almost in the fully closed position and latch member 38 is at an unlatched limit position in its range of pivotal motion about latch pivot axis 41 relative to door 28. The unlatched limit position may be defined, for example, by engagement of an abutment portion 56 of latch member 38 with an abutment surface 58 of door 28, whereby further pivoting motion of latch member in one angular direction (e.g. the counter-clockwise direction in the view of FIG. 6A) is prevented. Latch member 38 has a first range of pivotal motion about latch pivot axis 41 in a latching direction (e.g. clockwise in the view of FIG. 6A) for causing latch member 38 to engage with latch pin 42 to secure pump door 28 in the closed position, and a second range of pivotal motion about latch pivot axis 41 in the latching direction for causing latch member 38 to actuate free-flow protection device 16 against the bias of spring 48 to unpinch the resilient tubing 15 and allow fluid flow through the tubing.

Figure 6B:
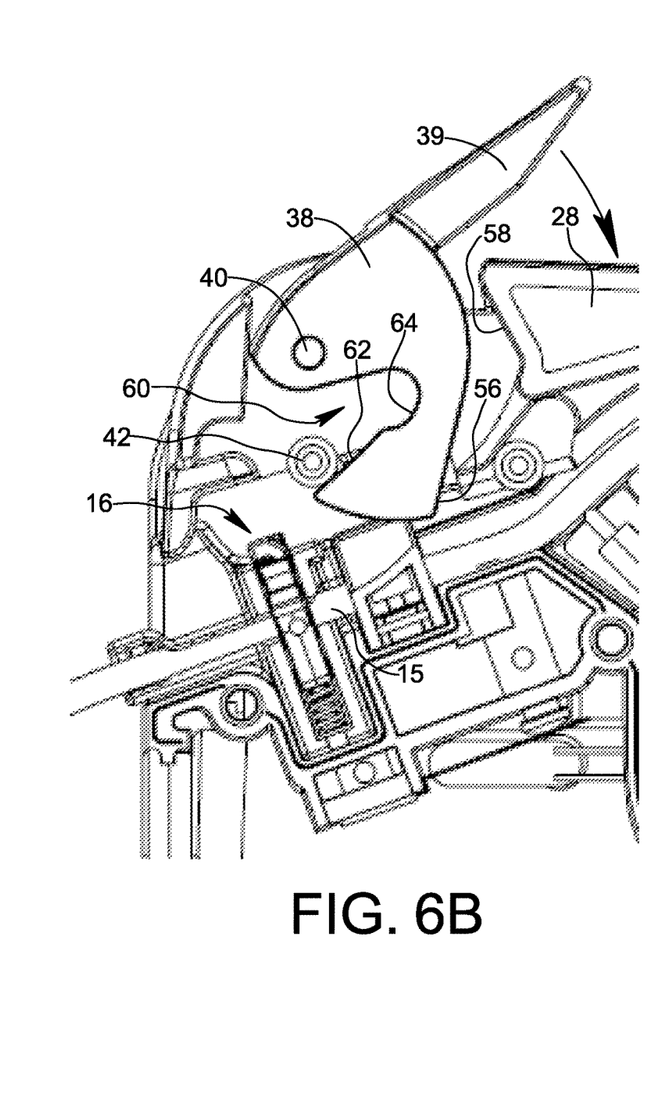
Figure 6C:
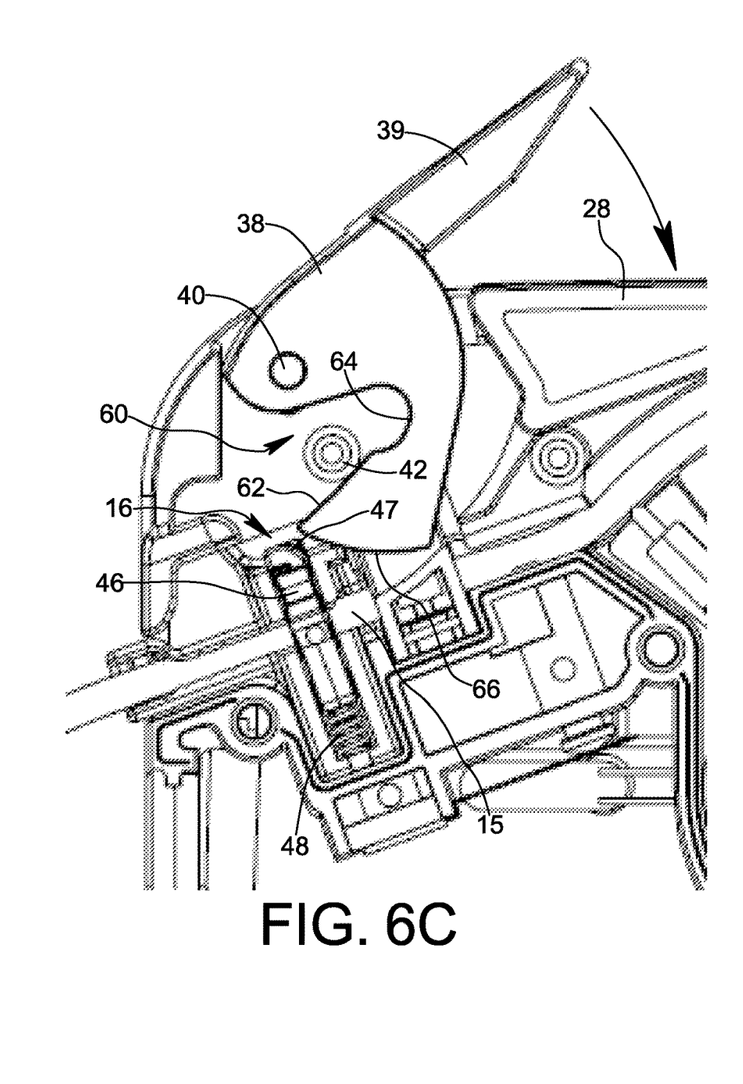
Figure 6D:
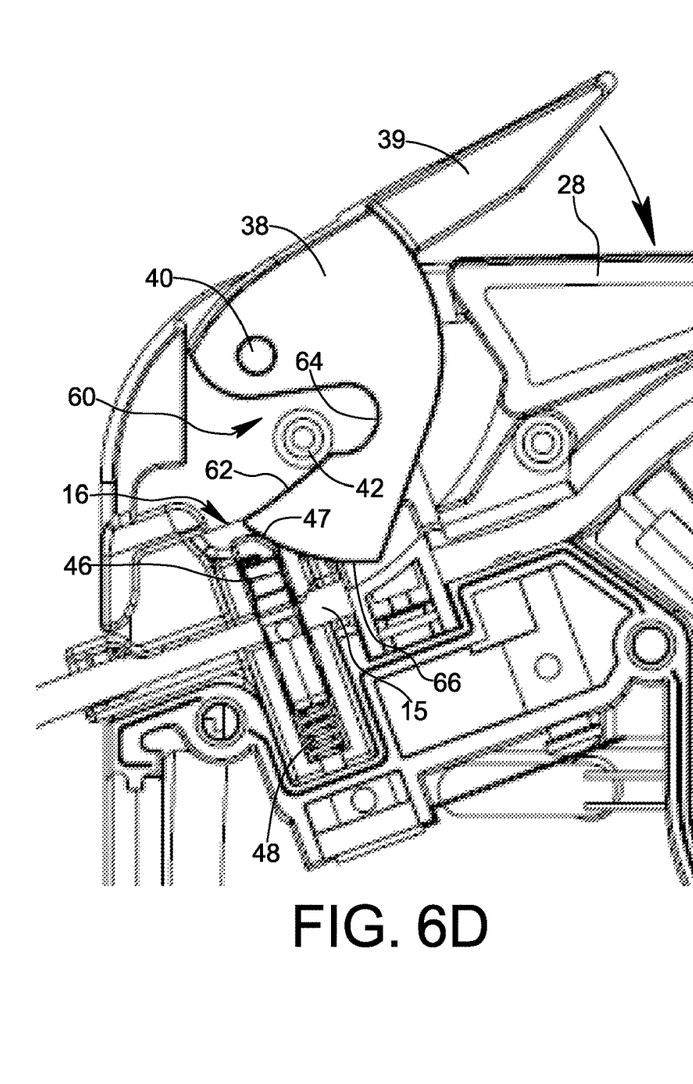
Figure 6E:
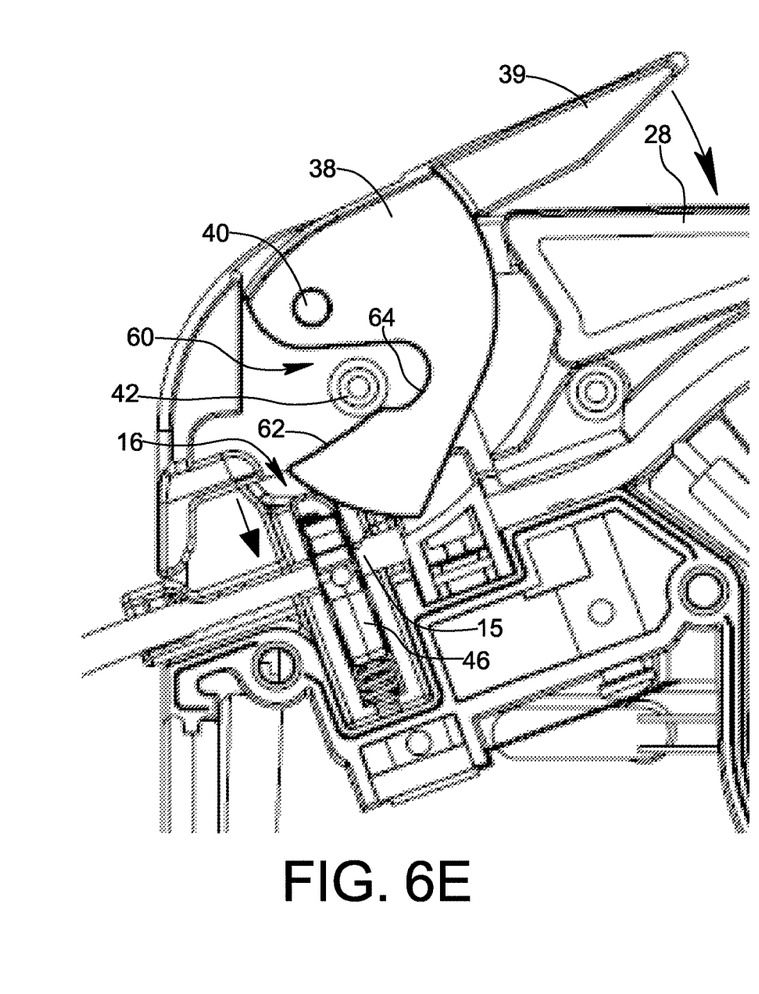
Figure 6F:
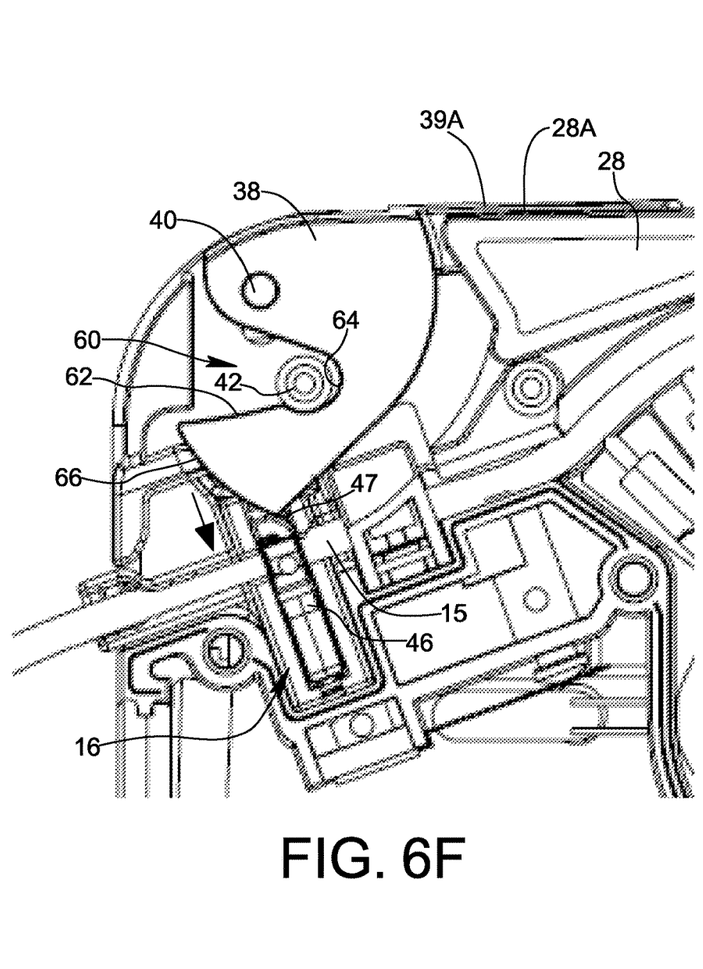

The first range of pivotal motion of latch member 38 is illustrated by FIGS. 6A-6F. Latch member 38 includes a handle or stem 39 which facilitates manual pivoting of the latch member about latch pivot axis 41. Latch member 38 further includes a slot 60 having an entryway surface 62 leading to a keyhole portion 64. When latch member 38 is at the unlatched limit position shown in FIG. 6A, entryway surface 62 of slot 60 is not yet in engagement with latch pin 42. As latch member 38 is pivoted in the latching direction about latch pivot axis 41, entryway surface 62 of slot 60 engages with latch pin 42 under the latch pin as shown in FIG. 6B. As latch member 38 is pivoted further in the latching direction, entryway surface 62 advances along underneath latch pin 42 to the position shown in FIG. 6C, thereby causing pump door 28 to pivot slightly more about the axis of hinge pin 30 to its fully closed position. Continued pivoting of latch member 38 in the latching direction as illustrated by FIGS. 6D and 6E brings keyhole portion 64 closely adjacent to latch pin 42 such that keyhole portion 64 is on the verge of receiving latch pin 42. Further pivoting of latch member 38 to the position shown in FIG. 6F causes keyhole portion 64 to receive latch pin 42, thereby securing pump door 28 in its closed position on infusion pump 10. The position of latch member 38 depicted in FIG. 6F may correspond with a latched limit position of latch member 38 at which latch member 38 is prevented from further pivotal motion in the latching direction by engagement of the latch member with pump door 28, wherein the latched limit position defines an end of the first range of pivotal motion. As shown in FIG. 6F, latch handle 39 may be configured such that a top surface 39A of latch handle 39 is substantially flush with a top surface 28A of pump door 28 when latch member is in the latched limit position.

The second range of pivotal motion of latch member 38 for actuating free-flow protection device 16 is illustrated by FIGS. 6D-6F. As seen in FIG. 6D, latch member 38 may include a curved cam surface 66 for cooperating with curved actuating surface 47 of plunger 46. In the pivotal position of latch member 38 shown in FIG. 6D, curved cam surface 66 makes contact with curved actuating surface 47 of plunger 46, thereby defining a beginning of the second range of pivotal motion of latch member 38. As latch member 38 is pivoted further in the latching direction about latch pivot axis 41 to the position shown in FIG. 6E, engagement of curved cam surface 66 with curved actuating surface 47 starts to displace plunger 46 downward relative to body 44 against the bias of spring 48. Continued pivoting of latch member 38 in the latching direction to the position shown in FIG. 6F causes further displacement of plunger 46 against the bias of spring 48 until tubing passageway 54 of plunger 46 and tubing guideway 50 of body 44 are substantially aligned with one another. As a result, tubing segment 15 is unpinched to allow fluid flow through the tubing in preparation for starting a pumping protocol. In the present embodiment, the latched limit position further defines an end of the second range of pivotal motion, however other arrangements are possible so long as latch member 38 pivots through at least a portion of the first range of pivotal motion before beginning to pivot through the second range of pivotal motion. At least a portion of the second range of pivotal motion may overlap with a portion of the first range of pivotal motion. The second range of pivotal motion may begin after latch member 38 has pivoted from the unlatched limit position through a predetermined angle about latch pivot axis 41 in the latching direction. It is advantageous if the predetermined angle is at least forty-five degrees to facilitate complete closure of door 28 prior to commencing actuation of free-flow protection device 16. For example, in the embodiment described herein, the second range of pivotal motion begins after latch member 38 has been pivoted through an angle of approximately fifty-three degrees from the unlatched limit position.

Administration set 12 may be unloaded from infusion pump 10 by pivoting latch member 38 in a reverse pivotal direction opposite to the latching direction from the latched limit position shown in FIG. 6F. As will be understood, this will allow plunger 46 to be displaced upward relative to body 44 by the bias of spring 48 to pinch tubing segment 15 before latch member 38 is disengaged from latch pin 42, thereby preventing free-flow from occurring when pump door 28 is unlatched and can be opened about the axis of hinge 30.

Figure 7:
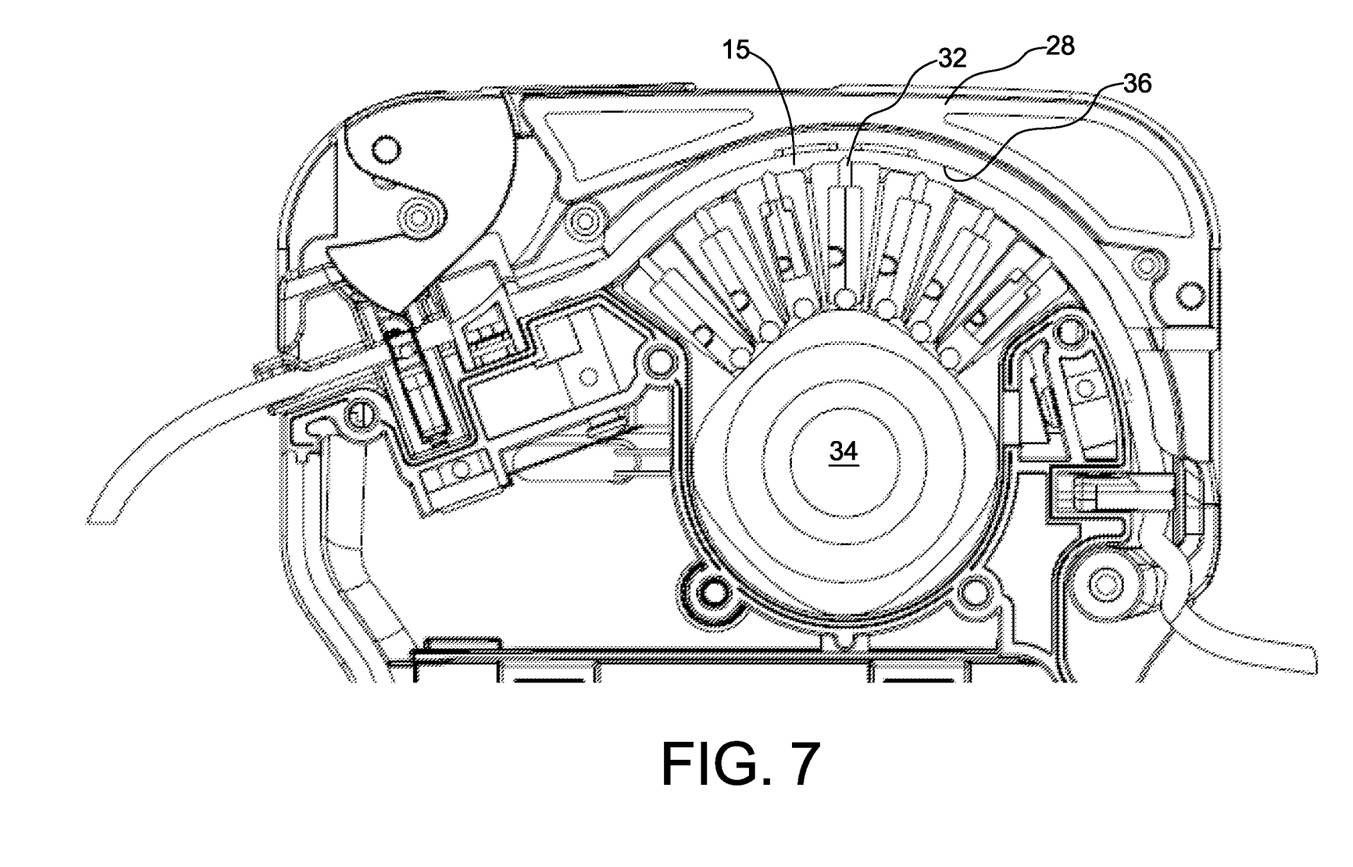
FIG. 7 is a zoomed out view corresponding to FIG. 6F showing occlusion of the tubing by one of the pumping fingers of the peristaltic infusion pump.

In another aspect of the present disclosure, a free-flow protection redundancy is provided. When pump door 28 is in the closed position shown in FIG. 7, at least one of the plurality of peristaltic pumping fingers 32 is arranged to pinch tubing 15 against platen surface 36 to prevent flow through the tubing when the pumping mechanism is not operating (i.e. motor-driven cam 34 is stationary).

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the claims.

What is claimed is:
1. An infusion pump apparatus comprising:
A) a length of resilient tubing;
B) an infusion pump including:
a pump housing;
a pumping mechanism supported by the pump housing;
a pump door movable relative to the pump housing, wherein the pump door moves to an open position to allow the length of tubing to be loaded in the infusion pump adjacent to the pumping mechanism and the pump door moves to a closed position covering the length of resilient tubing;
a latch member pivotally mounted to the pump door, wherein the latch member is pivotable relative to the pump door about a latch pivot axis; and
a latch pin at a fixed location relative to the pump housing; and
C) a free-flow protection device biased to pinch the resilient tubing closed to stop fluid flow therethrough;
wherein the latch member has a first range of pivotal motion about the latch pivot axis in a latching direction for causing the latch member to engage with the latch pin to secure the pump door in the closed position and a second range of pivotal motion about the latch pivot axis in the latching direction for causing the latch member to actuate the free-flow protection device against the bias to unpinch the resilient tubing and allow fluid flow therethrough, wherein the latch member pivots through at least a portion of the first range of pivotal motion before beginning to pivot through the second range of pivotal motion; and
wherein the pump door does not contact the free-flow protection device when the pump door is in the closed position.

2. The infusion pump apparatus according to claim 1, wherein at least a portion of the second range of pivotal motion overlaps with a portion of the first range of pivotal motion.

3. The infusion pump apparatus according to claim 1, wherein the latch member has an unlatched limit position defining a beginning of the first range of pivotal motion, and the second range of pivotal motion begins after the latch member has pivoted from the unlatched limit position through a predetermined angle about the latch pivot axis in the latching direction.

4. The infusion pump apparatus according to claim 1, wherein the pump door includes a platen surface and the pumping mechanism includes a plurality of peristaltic pumping fingers opposed by the platen surface when the pump door is in the closed position and a motor-driven cam operable to displace the plurality of peristaltic pumping fingers to resiliently deform the tubing against the platen surface, wherein at least one of the plurality of peristaltic pumping fingers is arranged to pinch the tubing against the platen surface to prevent flow through the tubing when the pump door is in the closed position and the pumping mechanism is not operating.

5. The infusion pump apparatus according to claim 1, wherein the latch member includes a curved cam surface and the free-flow protection device includes a curved actuating surface for cooperating with the curved cam surface, and wherein the curved cam surface engages the curved actuating surface while the latch member is pivoted through the second range of pivotal motion to actuate the free-flow protection device.

6. The infusion pump apparatus according to claim 1, wherein the latch member includes a slot having a keyhole portion and an entryway surface leading to the keyhole portion, and wherein the entryway surface and then the keyhole portion sequentially engage with the latch pin as the latch member is pivoted through the first range of pivotal motion.

7. The infusion pump apparatus according to claim 1, wherein the free-flow protection device is attached to the length of resilient tubing.

8. The infusion pump apparatus according to claim 3, wherein the predetermined angle is at least forty-five degrees.

9. The infusion pump apparatus according to claim 3, wherein the latch member has a latched limit position at an end of the first range of pivotal motion, wherein the latched limit position further defines an end of the second range of pivotal motion.

10. An infusion pump apparatus comprising:
A) a length of resilient tubing;
B) an infusion pump including:
a pump housing;
a pumping mechanism supported by the pump housing;
a pump door movable relative to the pump housing, wherein the pump door moves to an open position to allow the length of tubing to be loaded in the infusion pump adjacent to the pumping mechanism and the pump door moves to a closed position covering the length of resilient tubing;
a latch member pivotally mounted to the pump door, wherein the latch member is pivotable relative to the pump door about a latch pivot axis; and
a latch pin at a fixed location relative to the pump housing; and
C) a free-flow protection device biased to pinch the resilient tubing closed to stop fluid flow therethrough;
wherein the latch member has a first range of pivotal motion about the latch pivot axis in a latching direction for causing the latch member to engage with the latch pin to secure the pump door in the closed position and a second range of pivotal motion about the latch pivot axis in the latching direction for causing the latch member to actuate the free-flow protection device against the bias to unpinch the resilient tubing and allow fluid flow therethrough, wherein the latch member pivots through at least a portion of the first range of pivotal motion before beginning to pivot through the second range of pivotal motion; and
wherein the latch member includes a curved cam surface and the free-flow protection device includes a curved actuating surface for cooperating with the curved cam surface, and wherein the curved cam surface engages the curved actuating surface while the latch member is pivoted through the second range of pivotal motion to actuate the free-flow protection device.

11. The infusion pump apparatus according to claim 10, wherein at least a portion of the second range of pivotal motion overlaps with a portion of the first range of pivotal motion.

12. The infusion pump apparatus according to claim 10, wherein the latch member has an unlatched limit position defining a beginning of the first range of pivotal motion, and the second range of pivotal motion begins after the latch member has pivoted from the unlatched limit position through a predetermined angle about the latch pivot axis in the latching direction.

13. The infusion pump apparatus according to claim 10, wherein the pump door does not contact the free-flow protection device when the pump door is in the closed position.

14. The infusion pump apparatus according to claim 10, wherein the pump door includes a platen surface and the pumping mechanism includes a plurality of peristaltic pumping fingers opposed by the platen surface when the pump door is in the closed position and a motor-driven cam operable to displace the plurality of peristaltic pumping fingers to resiliently deform the tubing against the platen surface, wherein at least one of the plurality of peristaltic pumping fingers is arranged to pinch the tubing against the platen surface to prevent flow through the tubing when the pump door is in the closed position and the pumping mechanism is not operating.

15. The infusion pump apparatus according to claim 10, wherein the latch member includes a slot having a keyhole portion and an entryway surface leading to the keyhole portion, and wherein the entryway surface and then the keyhole portion sequentially engage with the latch pin as the latch member is pivoted through the first range of pivotal motion.

16. The infusion pump apparatus according to claim 10, wherein the free-flow protection device is attached to the length of resilient tubing.

17. The infusion pump apparatus according to claim 12, wherein the predetermined angle is at least forty-five degrees.

18. The infusion pump apparatus according to claim 12, wherein the latch member has a latched limit position at an end of the first range of pivotal motion, wherein the latched limit position further defines an end of the second range of pivotal motion.

* * * * *